(12) United States Patent
Laugharn, Jr.

(10) Patent No.: US 10,168,258 B2
(45) Date of Patent: Jan. 1, 2019

(54) SAMPLE HOLDER FOR ACOUSTIC TREATMENT

(71) Applicant: Covaris, Inc., Woburn, MA (US)

(72) Inventor: James A. Laugharn, Jr., Boston, MA (US)

(73) Assignee: Covaris, Inc., Woburn, MA (US)

( * ) Notice: Subject to any disclaimer, the term of this patent is extended or adjusted under 35 U.S.C. 154(b) by 0 days.

(21) Appl. No.: 15/480,556

(22) Filed: Apr. 6, 2017

(65) Prior Publication Data

US 2017/0299481 A1   Oct. 19, 2017

Related U.S. Application Data

(60) Provisional application No. 62/322,420, filed on Apr. 14, 2016.

(51) Int. Cl.
*G01N 1/28* (2006.01)
*G01N 1/40* (2006.01)

(52) U.S. Cl.
CPC ........... *G01N 1/286* (2013.01); *G01N 1/4077* (2013.01); *G01N 2001/4088* (2013.01)

(58) Field of Classification Search
CPC ...................................................... G01N 1/286
See application file for complete search history.

(56) References Cited

U.S. PATENT DOCUMENTS 8,459,121 B2   1/2013   Laugharn, Jr. et al.
9,320,995 B2   4/2016   Laugharn, Jr. et al.

*Primary Examiner* — Bin Shen
(74) *Attorney, Agent, or Firm* — Wolf, Greenfield & Sacks, P.C.

(57) ABSTRACT

A sample holder and method for separating components of a viscous sample, such as a sputum sample, in a vessel having a porous element. Liquid may be flowed through the vessel during acoustic energy treatment, which may disrupt the viscous sample. Smaller components of the sample may pass through the porous element with liquid introduced into the vessel. Larger components, such a microbes, may be captured by the porous element and may remain intact and viable for subsequent analysis. The porous element may be removable from the vessel to recover the microbes.

16 Claims, 3 Drawing Sheets

SAMPLE HOLDER FOR ACOUSTIC TREATMENT

CROSS REFERENCE TO RELATED APPLICATION

This application claims the benefit of U.S. Provisional Application No. 62/322,420, filed Apr. 14, 2016, which is hereby incorporated by reference in its entirety.

BACKGROUND

Field of the Invention

Systems and methods for collecting, storing and/or treating biological samples such as sputum or blood are generally disclosed.

SUMMARY

The inventor has appreciated that many biological samples include multiple components that can often be difficult to separate from each other, e.g., for analysis of one or more components of the sample. For example, sputum samples taken from the lungs of a patient may contain fungal spores or cells, or other potentially harmful microbes that may need to be studied, e.g., to determine if the patient has a dangerous infection. However, separating components of such sputum samples can be difficult, e.g., because of its viscous nature, the sample may resist separation of microbes from remaining portions of the sample while maintaining the microbes intact. Additionally, microbes may be very dilute (e.g., 1 microbe in 10 ml of a blood sample) and therefore, separation of the microbes from the sample may be difficult.

Aspects of the invention provide a sample holder and method to separate components of samples, including highly viscous or other sample types that resist separation of components due to one characteristic or another. In one embodiment, a sample holder includes a vessel having a loading opening that allows access to an interior space, e.g., to allow a sample to be placed into the interior space. A cover may be arranged for positioning at the loading opening in a closed position to seal the loading opening closed. A substrate mount may be provided in the interior space, and an inlet may provide fluid to the interior space, while an outlet is arranged to receive fluid from the interior space. The substrate mount may removably engage with a porous element so that the porous element separates an inlet side of the interior space from an outlet side of the interior space. That is, the inlet side of the interior space may be in fluid communication with the inlet, and the outlet side of the interior space may be in fluid communication with the outlet. The porous element and the substrate mount may be arranged so that with the porous element engaged with the substrate mount, any fluid in the interior space must pass through the porous element to move between the inlet side and outlet side of the interior space.

Focused acoustic energy may disrupt or otherwise treat a sample in the inlet side of the interior space, e.g., to solubilize, liquefy or otherwise reduce a viscosity of the sample. Liquid, such as a buffer solution, may be introduced into the inlet of the vessel so that liquid flows through the porous element and to the outlet of the vessel. As a result, smaller size portions of the disrupted sample may pass through the porous element to the outlet of the vessel, while larger size portions of the disrupted sample cannot pass through the porous element and so remain in the inlet side of the interior space or are captured by the porous element. In one embodiment, the porous element may have pores arranged to prevent the passage of fungal spores or cells from passing through the porous element so that any fungal spores or cells in a sputum sample remain in the inlet side of the interior space or are captured by the porous element. The porous element may be arranged to prevent the passage of other microbes in the sample, e.g., by suitably sizing pores of the porous element. In some cases, pore sizes of 1-20 microns may be suitable, and yet in other cases a pore size of 0.2 to 0.45 microns may be required to prevent the passage of particular microbes.

In some cases, microbes captured by the porous element may be recovered by removing the porous element from the vessel. That is, in some embodiments, the acoustic energy used to disrupt the sample, e.g., to reduce its viscosity, may be arranged to prevent lysis or other destruction of the microbes, e.g., the microbes may remain alive or otherwise viable for culturing or other study. Accordingly, intact, viable microbes may be removed from the vessel with the porous element after a sample has been treated. After removal of the porous element from the vessel, microbes may be separated from the porous element in different ways, such as by immersing the porous element in a suitable liquid and exposing the porous element to focused acoustic energy suitable to separate the microbes from the porous element. The microbes may be lysed in this subsequent acoustic treatment or recovered in intact, and viable condition, e.g., for culturing.

In other cases, microbes captured or prevented passage by a porous element may be subsequently treated in the vessel using acoustic energy with one or more different parameters than that used to solubilize, liquefy or otherwise disrupt the initially viscous sample. For example, once a sample has been suitably disrupted to separate smaller size portions, which pass through the porous element, from larger size portions, which are retained by the porous element, the retained larger size material may be treated with acoustic energy suitable to lyse microbes or other cells in the retained material. This lysing treatment may release desired biomarkers, such as biomolecules, which may be retained by the porous element, or may pass through the porous element with flow of liquid to exit the vessel. These biomarkers may be collected and used for subsequent analysis. By first separating microbes or other material to be isolated from other portions of a sample, and then specifically treating the separated microbes or other material with a different acoustic energy, a same vessel may be used to not only separate sample portions from each other, but also lyse or otherwise process a selected portion for collection of biomarkers or other components.

In some embodiments, the interior space of the vessel may have a volume of 2 ml to 10 ml, and a volume of liquid, such as a buffer solution, that is larger than the volume of the interior space may be introduced into the vessel via the inlet to help separate portions of the sample from each other. In some cases, the volume of liquid introduced into the vessel may be 10 ml to 100 ml or more, and may be done during or after acoustic treatment. While the vessel may have different arrangements, in one embodiment, the vessel has a tapered shape that has a widest portion near the loading opening and has a narrowest portion near the outlet. For example, the vessel may have a frusto-conical shape with a widest portion located where the cover engages the vessel. The substrate mount may be located nearer to the narrowest portion than to the widest portion, e.g., so that the inlet side of the interior space has a larger volume than the outlet side.

The inlet may be positioned nearer the widest portion of the vessel than to the narrowest portion, e.g., near the loading opening, and the outlet may be located at the narrowest portion. In some cases, the porous element has a disc shape, but may be arranged in other ways, such as a partial spherical shell, cone, sheet, or other. The cover may have an acoustic window to pass acoustic energy to the interior space. For example, an acoustic energy source used to generate the acoustic energy that treats the sample may be positioned remote from the vessel and the acoustic energy may be transmitted via a coupling medium to the vessel. The acoustic energy may pass through the cover and into the interior space to treat the sample.

In one embodiment, a method for treating a sample with acoustic energy includes providing a vessel having a loading opening that allows access to an interior space of the vessel, and providing a sample in the inlet side of an interior space of the vessel via the loading opening. The vessel may also have a substrate mount in the interior space engaged with a porous element, an inlet to provide fluid to an inlet side of the interior space, and an outlet to receive fluid from an outlet side of the interior space. The porous element may be removably engaged with the substrate mount and be positioned in the vessel to separate the inlet side of the interior space from the outlet side of the interior space such that any fluid in the interior space must pass through the porous element to move between the inlet side and outlet side of the interior space. A cover may be positioned at the loading opening in a closed position to seal the loading opening closed, and a flow of liquid may be provided into the inlet of the vessel so as to cause flow of liquid from the inlet side through the porous element to the outlet side of the interior space and to the outlet of the vessel. Acoustic energy may be provided to expose the sample to a focal zone of acoustic energy while located in the inlet side of the interior space. As mentioned above, the acoustic energy may be arranged to disrupt the sample, e.g., to reduce the sample's viscosity and disperse components of the sample in the liquid. Also, in some cases, microbes in the sample, such as fungal spores or cells, bacteria, etc., may remain viable and/or intact. As a result, sufficiently small size portions of the disrupted sample may pass through the porous element with liquid that passes through the porous element to the outlet, and sufficiently large size portions, such as microbes, of the disrupted sample may remain in in the inlet side of the interior space or be captured by the porous element.

In some cases, the sample may include fungal spores or cells, and the porous element may have pores arranged to prevent the passage of fungal spores or cells from passing through the porous element. The interior space may have a volume of 2 ml to 10 ml in some cases, though smaller volumes of 2 ml to 500 microliters or less are possible, and a volume of liquid from 10 ml to 100 ml may be provided into the inlet.

In some embodiments, a focal zone of the acoustic energy may be positioned near the porous element to aid in passage of sufficiently small portions of the sample through the porous element. That is, positioning the focal zone near the porous element may aid in disrupting viscous portions of the sample near or at the porous element that might otherwise impede the flow of liquid through the porous element. As a result, the acoustic energy may aid in maintaining flow through the porous element. As noted above, in some cases the sample may include a sputum sample with fungal spores and/or cells or other microbes. In other cases, the sample may include a blood sample with pathogenic microbes and/or other foreign cells. The acoustic energy used to disrupt the sample(s) may be arranged to avoid lysing the fungal spores or cells, or other pathogenic microbes in the sample. In some embodiments, the porous element may be removed from the vessel after exposing the sample to acoustic energy to recover larger portions of the sample, such as microbes that are captured by the porous element.

Other advantages and novel features of the present disclosure will become apparent from the following detailed description of various non-limiting embodiments when considered in conjunction with the accompanying figures and claims. For example, while the extraction of certain types of cells or biomolecules is discussed herein, a variety of different compounds may be recovered from a sample, including metabolites and/or other compounds included in blood.

BRIEF DESCRIPTION OF THE DRAWINGS

Aspects of the present disclosure are described with reference to the following drawings in which numerals reference like elements, and wherein.

DETAILED DESCRIPTION

Figure 1:
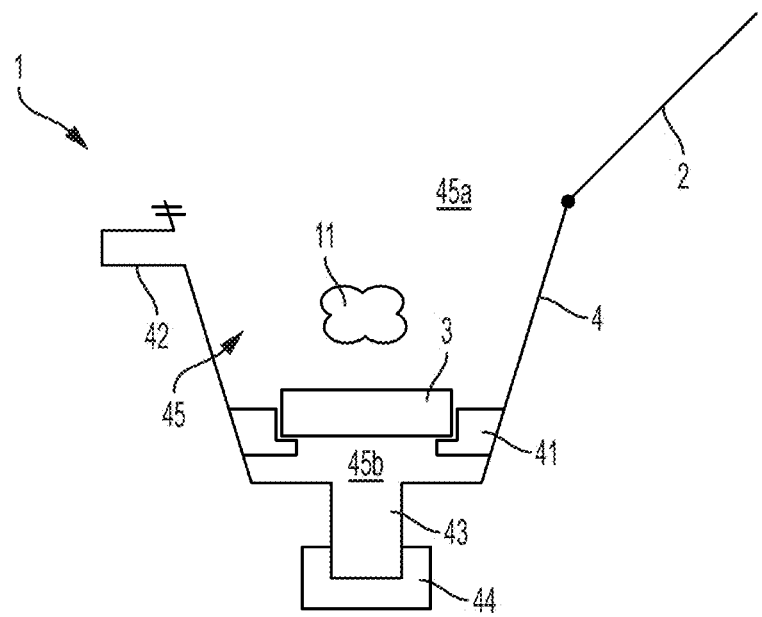
FIG. 1 shows a cross-sectional view of a sample holder including a cover and a porous element in an illustrative embodiment.

Aspects of the present disclosure are not limited in application to the details of construction and the arrangement of components set forth in the following description or illustrated in the drawings. Other embodiments may be employed and aspects of the present disclosure may be practiced or be carried out in various ways. Also, the phraseology and terminology used herein is for the purpose of description and should not be regarded as limiting.

FIG. 1 shows an illustrative embodiment of a sample holder 1 that includes a vessel 4 with a cover 2 and has an internal space 45 into which a sample 11 may be provided. The cover 2 may be moved from an open position shown in FIG. 1 to a closed position in which the cover 2 engages the vessel 4 at a loading opening to seal the interior space 45 closed. The vessel 4 also includes a substrate mount 41 that is arranged to removably engage with a porous element 3. In this embodiment, the substrate mount 41 includes an annular shelf that supports a disc shaped porous element 3 and engages with the porous element 3 by an interference fit. However, the porous element 3 may be arranged in other ways, e.g., to have different shapes, and the substrate mount 41 may correspondingly vary in shape or arrangement. In short, the substrate mount 41 and porous element 3 are arranged to separate an inlet side 45a from an outlet side 45b of the interior space 45 such that any liquid must pass through the porous element 3 to move between the inlet side 45a and the outlet side 45b of the interior space 45.

The vessel 4 also includes an inlet 42 to introduce liquid or other fluid into the interior space 45 and an outlet 43 to receive liquid or other fluid from the interior space 45. In some embodiments, a sample 11 may be introduced into the interior space 45 through the inlet 42. The sample 11 may be introduced via the inlet 42 in its original, unchanged condition, or may be diluted or mixed with a liquid such as a buffer solution. In such cases, the cover 2 may be eliminated, or may be retained and not used for introducing the sample 11. Instead, the cover 2 may be opened only to retrieve a porous element 3. A cap 44 is shown covering the outlet 43, and a similar cap may be provided for the inlet 42 if desired. The cap 44 may prevent unwanted leakage of fluid from the interior space 45 prior to or after acoustic treatment. In this embodiment, the vessel 4 has a tapered shape, e.g., a frustoconical shape, and the inlet 42 is positioned nearer the widest portion of the tapered shape than the narrowest portion, while the outlet 43 is positioned nearer the narrowest portion than the widest portion. This arrangement may aid in positioning the sample 11 in the vessel 4 (e.g., by providing a relatively wide loading opening), while helping direct flow into a smaller area where the porous element 3 is located. However, the vessel 4 need not have a tapered shape, and/or the inlet 42 and outlet 43 may be positioned in other ways, e.g., in the cover 2. In some embodiments, the sample holder 1 may be arranged to be used only a single time, and may be provided initially in a sterile form so that sample treatment results are not contaminated by foreign material.

Figure 2:
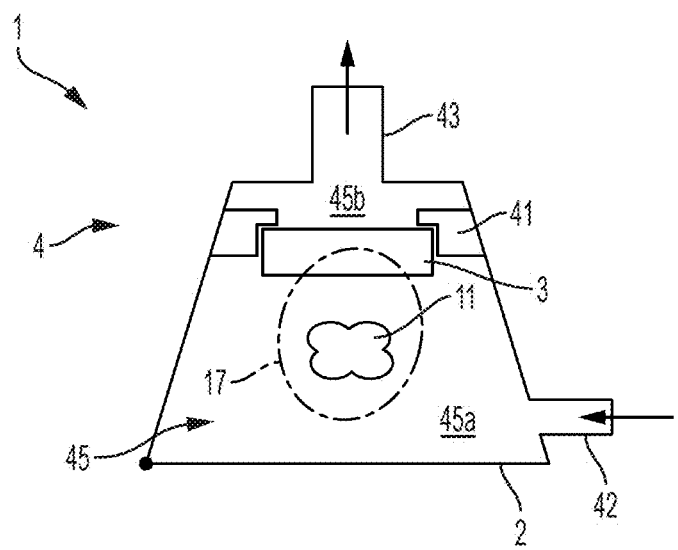
FIG. 2 shows a cross-sectional view of the FIG. 1 sample holder in an inverted orientation.

With a sample 11 in the interior space 45, the cover 2 may be closed and the vessel 4 inverted as shown in FIG. 2 to treat the sample with focused acoustic energy. The cover 2 may have an acoustic window that allows acoustic energy to pass and create a focal zone 17 of acoustic energy in the interior space 45. As mentioned above, the focal zone 17 may be located near the porous element 3 (e.g., so the focal zone 17 partially overlaps the porous element 3) so as to aid in flow through the porous element 3. During acoustic energy treatment, liquid may be provided into the inlet 42 so that liquid flows through the porous element 3 and to the outlet 43. Relatively small components of the sample 11 that pass through the porous element 3 and exit the outlet 43 may be recovered for analysis. Also, relatively larger components of the sample 11 that cannot pass through the porous element 3 or are captured by the porous element 3 may be recovered as well, e.g., by removing the remaining sample 11 and/or the porous element 3 from the vessel 4. The acoustic energy may be arranged to leave microbes or other cells intact, and so recovered microbes may be viable, e.g., for culturing or other analysis processes. In some cases, the acoustic energy may be arranged to achieve differential lysis such that some cells are lysed, while others are not. For example, where a sample includes a blood sample having red blood cells and other mammalian cells along with microbial cells, the acoustic energy may lyse the mammalian cells but leave microbial cells intact. The lysed mammalian cell components may pass through the porous element 3 and exit via the outlet 43, while the intact microbial cells may be captured by the porous element 3. Thus, in some embodiments, the acoustic energy and porous element 3 may be arranged to lyse certain cells, but not others, and material from lysed cells may pass through the porous element 3 while un-lysed cells do not pass the porous element 3.

Intact cells or other material that do not pass a porous element 3 may be recovered, e.g., by removing the porous element 3 and captured material from the vessel 4. The porous element 3 and captured material may be placed in another treatment vessel, and the porous element 3 and captured material again treated with acoustic energy. However, in this second treatment, the acoustic energy and/or liquid provided with the porous element 3 in the treatment vessel (e.g., a lysing buffer) may be arranged to lyse the intact cells and suitably stabilize biomarkers released from the lysed cells for later analysis.

Figure 3:
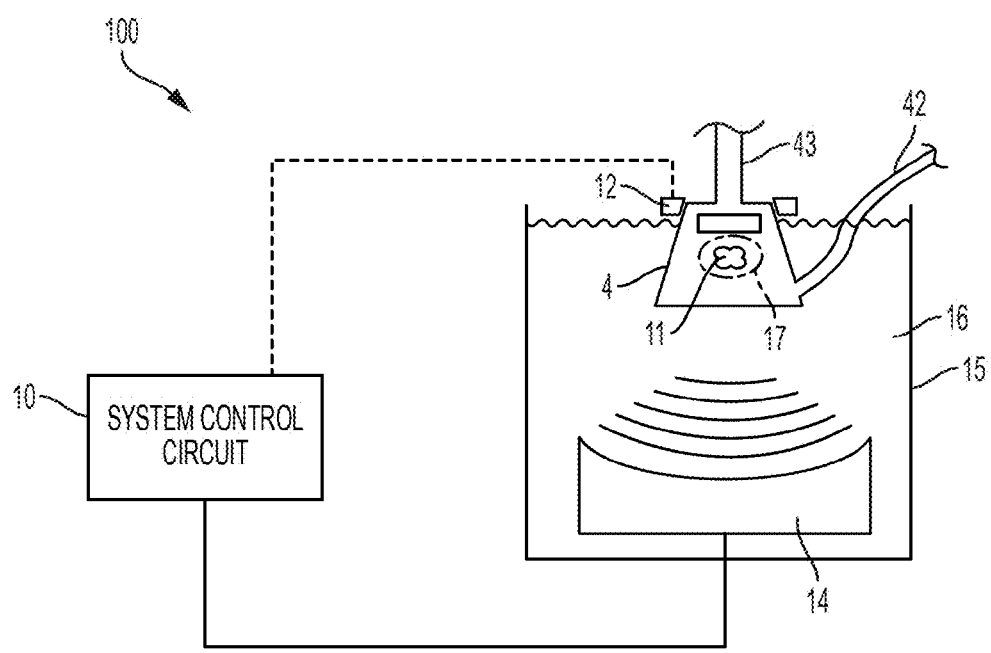
FIG. 3 shows a schematic block diagram of an acoustic treatment system that incorporates one or more aspects of the present disclosure.

FIG. 3 shows a schematic block diagram of an acoustic treatment system 100 that incorporates one or more aspects of the present disclosure and/or can be employed with one or more aspects of the sample holder described herein. It should be understood that although embodiments described herein may include most or all aspects of the invention(s), aspects of the invention(s) may be used alone or in any suitable combination with other aspects of the invention(s).

In this illustrative embodiment, the acoustic treatment system 100 includes an acoustic energy source with an acoustic transducer 14 (e.g., including one or more piezoelectric elements) that is capable of generating an acoustic field (e.g., at a focal zone 17) suitable to cause mixing, e.g., caused by cavitation, and/or other effects on a sample 11 contained in a vessel 4. The sample 11 may include solid particles, and/or liquid material and/or a combination of liquid and solid material. Acoustic energy may be transmitted from the transducer 14 to the vessel 4 through a coupling medium 16, such as a liquid (e.g., water), a gel or other semi-solid, or a solid, such as a silica, metal or other material. Where the coupling medium 16 is a liquid, a coupling medium container 15 may be used to hold the coupling medium 16.

The vessel 4 may be arranged as discussed above and may be supported at a location by a vessel holder 12. Although a vessel holder 12 is not necessarily required, the vessel holder 12 may interface with the control circuit 10 so that the vessel 4 and the sample 11 in the vessel is positioned in a known location relative to an acoustic field, for example, at least partially within a focal zone 17 of acoustic energy. The vessel 4 may be formed of glass, plastic, metal, composites, and/or any suitable combinations of materials, and formed by any suitable process, such as molding, machining, stamping, and/or a combination of processes.

The transducer 14 can be formed of a piezoelectric material, such as a piezoelectric ceramic. In some embodiments, the ceramic may be fabricated as a "dome," which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing or undamped to increase power output. The response may be linear if not overdriven. The high-energy focus zone of one of these domes may be cigar-shaped. At 1 MHz, the focal zone is about 6 cm long and about 2 cm wide for a 20 cm dome, or about 15 mm long and about 3 mm wide for a 10 cm dome. The peak positive pressure obtained from such systems is about 1 MPa (mega Pascal) to about 10 MPa pressure, or about 150 PSI (pounds per square inch) to about 1500 PSI, depending on the driving voltage. The focal zone 17, defined as having an acoustic intensity within about 6 dB of the peak acoustic intensity, may be formed around the geometric focal point of the transducer 14. It is also possible to generate a line-shaped focal zone, e.g., that spans the width of a multi-well plate and enables the system 100 to treat multiple samples simultaneously. Other arrangements for producing focused acoustic energy are possible. For example, a flat transducer may be provided with a tapered waveguide for focusing or otherwise channeling acoustic energy emitted from the transducer toward a relatively small space where the sample and vessel are located.

To control an acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. Moreover, the system control circuit 10 may control various other acoustic treatment system 100 functions, such as positioning of the vessel 4 and/or acoustic transducer 14, receiving operator input (such as commands for system operation), outputting information (e.g., to a visible display screen, indicator lights, sample treatment status information in electronic data form, and so on), and others. Thus, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

Under the control of a control circuit 10, the acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample. The focal zone 17 may be larger than the sample volume, or may be smaller than the sample volume, as shown in FIG. 3. U.S. Pat. Nos. 6,948,843 and 6,719,449 are incorporated by reference herein for details regarding the construction and operation of an acoustic transducer and its control. A focal zone is an area where the intensity of the acoustic energy is within 6 dB of the maximum intensity.

A sample may be treated with acoustic energy using the arrangement of FIG. 3 as discussed above. For example, with a sputum sample 11 in the vessel 4, the cover 2 may be closed and the vessel 4 inverted and positioned in a liquid coupling medium 16 so the cover 2 is below a surface of the medium 16. Thus, in an as-used position to treat a sample with acoustic energy, the vessel 4 may be arranged so that the inlet 42 is positioned below the porous element 3, and so that the porous element 3 is positioned below the outlet 43. Or, in other words, the inlet side 45a of the interior space 45 may be positioned below the porous element 3, and the porous element 3 may be positioned below the outlet side 45b of the interior space. In this arrangement, flow of liquid through the vessel may be in an upward direction from the inlet 42 or inlet side 45a to the outlet 43 or outlet side 45b. Acoustic energy generated by the transducer 14 may pass through the cover 2, which may have an acoustic window that is transparent to acoustic energy, to form the focal zone 17 within the sample 11. Liquid, such as a buffer solution, may be provided into the interior space 45 via the inlet 42. The liquid may be provided by gravity flow, pump driven flow, or other, and at any suitable flow rate. In some cases, 10-100 ml of liquid may be introduced into the vessel over a 30 second to 2 minute treatment time, and the vessel may have a 2 ml-10 ml volume. As described above, the acoustic energy may disrupt the sample 11 so that relatively small portions of the sample pass through the porous element 3 and exit the vessel with the liquid. Other larger portions may remain in the inlet side 45a of the interior space 45 and/or may be captured by the porous element 3.

In an embodiment where the acoustic treatment system 100 is a Covaris S220 or E220 model and the sample 11 is a sputum sample containing fungal spores or cells to be recovered, acoustic treatment may be applied using a 50% duty cycle, a peak incident power of 100 watts, 200 cycles per burst, for a suitable period of time (e.g., 15 seconds or more). Of course, other duty cycles, peak power, cycles per burst and/or time periods may be used to produce a sufficient amount of power for processing the blood sample. For example, to achieve desirable results with regard to separation and recovery of components from a sample, the acoustic transducer may be operated at a peak intensity power of between 100 W and 300 W, a duty factor of between 10% and 90% and a cycles per burst of between 100 and 300, for an appropriate duration of time. It can be appreciated that the acoustic transducer may be operated so as to produce focused acoustic energy that results in a suitable level of energy input to the sample material.

Other vessel configurations are possible for separating components of a sample, such as a highly viscous sample. For example, in one embodiment, the sample holder may include a cylindrical tube into which a sputum or other sample is placed with a liquid, such as a buffer solution. A porous element may be placed in the vessel as well, and the porous element may be sized to closely contact the inner wall of the vessel. During or after acoustic treatment to solubilized, liquefy or otherwise disrupt the sample so as to disperse or separate its components, the porous element may be pushed downwardly into the vessel, e.g., to the bottom of the vessel. This action may cause flow of fluid from one side of the porous element to the other side so liquid and smaller portions of the sample to pass through the porous element, while larger portions such as microbes, may be captured in the porous element or remain in the vessel below the porous element. Liquid and sample components above the porous element may be removed, and subsequently the porous element may be recovered with any captured microbes or other larger sample portions.

Figure 4:
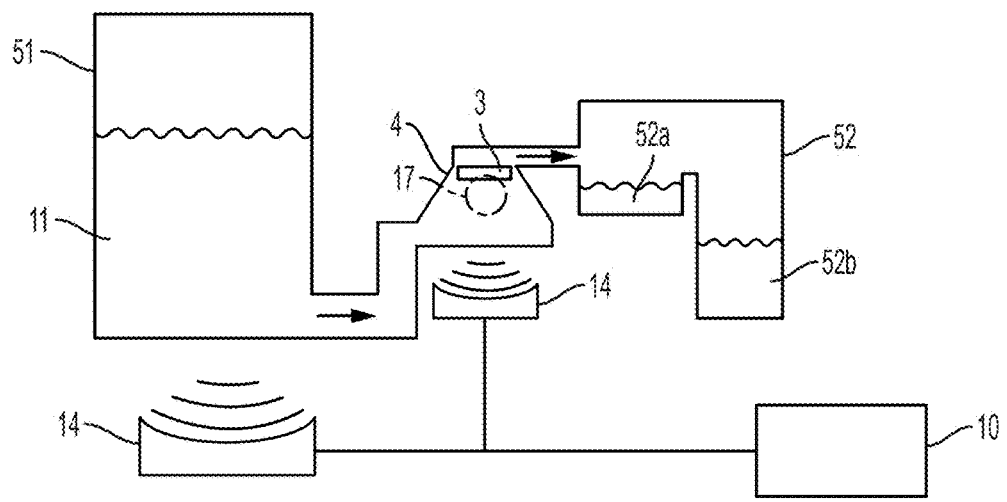
FIG. 4 shows a sample treatment apparatus in which a sample is treated with a first acoustic energy in a first sample holder, and the sample is treated with a second acoustic energy in a second sample holder.

FIG. 4 shows another embodiment for treating a viscous sample, such as a sputum sample, or other sample types in which the sample is solubilized, liquefied or otherwise disrupted in a first vessel 51 so as to reduce viscosity of the sample or break the sample into smaller constituent components. In this embodiment, a sputum sample 11 may be provided in the first vessel 51, optionally along with additional liquid such as a buffer solution. As discussed above, focused acoustic energy may be transmitted into the first vessel 51 to disrupt the sample. The disrupted sample, e.g., with reduced viscosity, may flow to a second vessel 4, which may be arranged in a way like that in FIGS. 1 and 2. However, in this embodiment, the vessel 4 does not have a removable cover 2 and the porous element 3 is not removable from the vessel 4, although those features may be retained in this embodiment if desired. The disrupted sample 11 may flow from the first vessel 51 to the second vessel 4 by gravity, pressure-based flow (e.g., where a pressure in the first vessel 51 is established to drive flow), by pump or other arrangement. Acoustic disruption of the sample 11 in the first vessel 51 and flow of the disrupted sample 11 to the second vessel 4 may continue until all or a desired portion of the sample 11 flows into/through the second vessel 4. As in the embodiments above, smaller size portions of the disrupted sample 11 may pass through the porous element 3 and into a third vessel 52 while larger size portions, such as microbes in a sputum sample, may be retained in the second vessel 4 by the porous element 3 (e.g., in the porous element 3 or upstream of the porous element 3 in the vessel 4). Although not required, acoustic energy may be employed in the second vessel 4 to aid in keeping the porous element 3 clear, i.e., so flow is not resisted in an undesired way. In some cases, acoustic energy in the second vessel 4 may additionally aid in disrupting the sample 11, e.g., to reduce its viscosity.

With a desired portion of the sample 11 having flowed into the second vessel 4, microbes or other larger size portions of the sample 11 may be concentrated in the vessel 4 since smaller size portions will have flowed through the porous element. This concentrated larger size material may be exposed to a second acoustic energy in the vessel 4, e.g., to lyse cells in the larger size material so that biomolecules and/or other biomarkers are released from the cells to pass through the porous element 3 and to the third vessel 52. Prior to this secondary acoustic treatment of the concentrated material, the third vessel 52 may be emptied of smaller size portions of the sample 11 that were collected earlier during the initial separation and concentration phase of the treatment operation. This way, biomarker material extracted from the concentrated microbes and other larger size material can be collected separate from the smaller size material. As noted above, liquid may be introduced into the vessel 4 during the secondary treatment of the concentrated material, such as a lysing solution, to aid in the lysing or other acoustic treatment as well as provide a flow to aid in the passage of biomarkers through the porous element 3. In some embodiments, the third vessel 52 may have a biomarker collection area 52a in which biomarkers may accumulate and a waste collection area 52b where other material may collect. In some embodiments, biomarker material may be heavier than other liquid, and so settle and collect in the collection area 52a while lighter liquid material may flow over a wall and into the collection area 52b. Concentrated biomarker material in the collection area 52a may be harvested and used for subsequent analysis, as is known in the art.

In some embodiments, the transducer may generate acoustic energy having a peak incident power over the course of a period of time that produces a particular amount of energy, to achieve preferred results. As described herein, the peak incident power (PIP) is the power emitted from the transducer during the active period of one cycle. The peak incident power, in some cases, may control the amplitude of the acoustic oscillations. The energy applied to the sample material may be determined from the peak incident power of the applied acoustic energy and the duration of the acoustic treatment period. In some embodiments, to suitably lyse cells and extract or otherwise operate on the target biomolecule(s) from a sample, the acoustic transducer may be operated so as to generate focused acoustic energy according to a peak incident power of greater than or equal to 50 Watts, greater than or equal to 100 Watts, greater than or equal to 150 Watts, greater than or equal to 200 Watts, greater than or equal to 250 Watts, greater than or equal to 300 Watts, or other values outside of these ranges.

The acoustic transducer may be operated at a suitable duty factor, in combination with other parameters, to generate focused acoustic energy that leads to preferred results. As described herein, the duty factor is the percentage of time in a cycle in which the transducer is actively emitting acoustic energy. For example, a duty factor of 60% refers to the transducer being operated in an "on" state 60% of the time, and in an "off" state 40% of the time. In some embodiments, in appropriately lysing cells and extracting/processing the target biomolecule(s) from a blood sample, the acoustic transducer may be operated at a duty factor setting of greater than or equal to 10%, greater than or equal to 20%, greater than or equal to 30%, greater than or equal to 40%, greater than or equal to 50%, greater than or equal to 60%, greater than or equal to 70%, or greater than or equal to 80%, or other values outside of these ranges.

The acoustic transducer may be operated according to a suitable cycles-per-burst setting to achieve preferred results. As described herein, the cycles per burst (CPB) is the number of acoustic oscillations contained in the active period of one cycle. In some embodiments, to lyse and extract/process the target biomolecule(s) from a blood sample, the acoustic transducer may be operated to generate focused acoustic energy according to a cycles per burst setting of greater than or equal to 50, greater than or equal to 100, greater than or equal to 150, greater than or equal to 200, or other values outside of these ranges.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the present disclosure have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the present disclosure.

The invention claimed is:

1. A method for treating a sample with acoustic energy, comprising:
    providing a vessel having a loading opening that allows access to an interior space of the vessel, the vessel having a substrate mount in the interior space engaged with a porous element, an inlet to provide fluid to an inlet side of the interior space, and an outlet to receive fluid from an outlet side of the interior space, the inlet is positioned below the porous element, and the porous element is positioned below the outlet wherein the flow from the inlet to the outlet is in an upward direction, the porous element removably engaged with the substrate mount so as to separate the inlet side of the interior space from the outlet side of the interior space such that any fluid in the interior space must pass through the porous element to move between the inlet side and outlet side of the interior space;
    loading a sample in the inlet side of an interior space of the vessel via the loading opening;
    closing the loading opening with a cover at the loading opening in a closed position;
    generating focused acoustic energy to expose and disrupt the sample at a focal zone of acoustic energy while in the inlet side of the interior space; and
    flowing a liquid into the inlet of the vessel so as to cause flow of liquid from the inlet side through the porous element to the outlet side of the interior space and to the outlet of the vessel;
    wherein the acoustic energy disrupts the sample such that sufficiently small size portions of the disrupted sample pass through the porous element with liquid that passes through the porous element to the outlet, and such that sufficiently large size portions of the disrupted sample remain in in the inlet side of the interior space or are captured by the porous element.

2. The method of claim 1, wherein the sample includes fungal spores or cells, and the porous element has pores arranged to prevent the passage of fungal spores or cells from passing through the porous element.

3. The method of claim 1, wherein the interior space has a volume of 2 ml to 10 ml, and the step of flowing a liquid includes inputting 10 ml to 100 ml of liquid into the inlet.

4. The method of claim 1, wherein the vessel has a tapered shape that has a widest portion near the loading opening and has a narrowest portion near the outlet.

5. The method of claim 4, wherein the substrate mount is located nearer to the narrowest portion than to the widest portion.

6. The method of claim 4, wherein the inlet is positioned nearer the widest portion than to the narrowest portion.

7. The method of claim 1, further comprising removing the porous element from the vessel after exposing the sample to the focal zone of acoustic energy to recover larger portions of the sample.

8. The method of claim 1, wherein the step of generating focused acoustic energy includes transmitting acoustic energy through the cover and into the interior space.

9. The method of claim 1, wherein the step of generating focused acoustic energy includes positioning the focal zone near the porous element to aid in passage of sufficiently small portions of the sample through the porous element.

10. The method of claim 1, wherein the sample includes a sputum sample including fungal spores and/or cells.

11. The method of claim 1, wherein the sample includes a blood sample including pathogenic microbes and/or other foreign cells.

12. The method of claim 1, further comprising adjusting the acoustic energy to avoid lysing fungal spores or cells, or pathogenic microbes in the sample.

13. A method for treating a sample with acoustic energy, comprising:
    providing a vessel having an interior space;
    providing a sample in the interior space of the vessel;
    providing a porous element in the vessel such that the porous element separates the interior space into a first side and a second side with the sample located in the first side, and such that any fluid must pass through the porous element to travel between the first and second sides, wherein the first side is positioned below the porous element, and the porous element is positioned below the second side such that flow from the first side to the second side is in an upward direction;
    generating focused acoustic energy to expose the sample to a focal zone of acoustic energy while in the first side of the interior space, the acoustic energy disrupting the sample to reduce a viscosity of the sample; and
    flowing a liquid from the first side to the second side of the interior space such that sufficiently small size portions of the disrupted sample pass through the porous element with liquid that passes through the porous element to the second side, and such that sufficiently large size portions of the disrupted sample remain in in the first side of the interior space or are captured by the porous element.

14. The method of claim 13, wherein the step of flowing a liquid includes flowing a liquid into an inlet of the vessel so as to cause flow of liquid from the first side through the porous element to the second side of the interior space.

15. The method of claim 13, wherein the focused acoustic energy is a first focused acoustic energy that is arranged to avoid lysing microbes in the sample, the method further comprising exposing large size portions of the disrupted sample to a second focused acoustic energy arranged to lyse microbes in the large size portions to cause the lysed microbes to release biomarkers.

16. The method of claim 15, wherein the released biomarkers flow through the porous element to the second side.

* * * * *